(12) United States Patent
Sedel

(10) Patent No.: US 10,328,059 B2
(45) Date of Patent: *Jun. 25, 2019

(54) METHOD FOR TREATING HEPATIC ENCEPHALOPATHY

(71) Applicant: MEDDAY PHARMACEUTICALS, Paris (FR)

(72) Inventor: Frédéric Sedel, Paris (FR)

(73) Assignee: MEDDAY PHARMACEUTICALS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/134,144

(22) Filed: Sep. 18, 2018

(65) Prior Publication Data

US 2019/0070150 A1 Mar. 7, 2019

Related U.S. Application Data

(63) Continuation of application No. 15/935,695, filed on Mar. 26, 2018, now Pat. No. 10,117,854, which is a continuation of application No. PCT/EP2017/069194, filed on Jul. 28, 2017.

(30) Foreign Application Priority Data

Jul. 29, 2016 (EP) .................... 16305989

(51) Int. Cl.
*A61K 31/4188* (2006.01)
*A61K 9/00* (2006.01)
*A61P 25/28* (2006.01)
*A23L 33/15* (2016.01)
*A61K 45/06* (2006.01)

(52) U.S. Cl.
CPC .......... *A61K 31/4188* (2013.01); *A23L 33/15* (2016.08); *A61K 9/0019* (2013.01); *A61K 9/0053* (2013.01); *A61K 45/06* (2013.01); *A61P 25/28* (2018.01)

(58) Field of Classification Search
CPC . A61K 31/4188; A61K 9/0019; A61K 9/0053
See application file for complete search history.

(56) References Cited

U.S. PATENT DOCUMENTS

| 5,814,650 A | * | 9/1998 | Della Valle | ........... C07D 495/04 514/387 |
| 10,117,854 B2 | * | 11/2018 | Sedel | ....................... A23L 33/15 |
| 2004/0219188 A1 | | 11/2004 | Comer et al. | |

FOREIGN PATENT DOCUMENTS

| DE | 20202562 U1 | 5/2002 |
| JP | H01 226814 | 9/1989 |

OTHER PUBLICATIONS

Bajaj, "Review Article: the modern management of hepatic encephalopathy", Aliment Pharmacol Ther, 31, 2010, 537-547.
Belafia et al., "Insuffisance hepatique aigue", Urgences 2012, Chapter 70, pp. 1-13.
Berlioux et al., "Encephalopathie hepatique", Post'U (2014), pp. 1-7.
Ferenci, "Hepatic encephalopathy" Gastroenterology Report, 5(2), 2017, pp. 138-147.
Francoz et al, "Hepatic encephalopathy: How to improve the management in the intensive care unit?", Reanimation (2007)16, pp. 498-503.
Frederick, "Current Concepts in the Pathophysiology and Management of Hepatic Encephalopathy", Gastroenterology & Hepatology, vol. 7, Issue 4, Apr. 2011, pp. 222-233.
Leke et al., "Impairment of the Organization of Locomotor and Exploratory Behaviors in Bile Duct-Ligated Rats", PLoS One, May 2012, vol. 7, Issue 5, pp. 1-8.
Nagamine et al., "Effect of biotin on ammonia and amino acid metabolism in urease-induced hyperammonaemic rats", Journal of Gastroenterology 86 (7) 1989, pp. 1519-1524.
Nagamine et al., "Effect of biotin on ammonia intoxication in rats and mice", J. Gastroenterol 1995: 30: pp. 351-355.
Sharma et al., "Management of Overt Hepatic Encephalopathy", Journal of Clinical and Experimental Hepatology, Mar. 2015, vol. 5, No. S1, pp. S82-S87.
Shawcross et al., "Systemic Inflammatory Response Exacerbates the Neuropsychological Effects of induced Hyperammonemia in Cirrhosis", Journal of Hepatology, Mar. 2004, 23 pages.
Chronic Liver Disease Foundation, Treatment of Overt Hepatic Encephalopathy: Focus on Outpatient Management, 24 pages., 2014.
Wright et al., "Endotoxemia Produces Coma and Brain Swelling in Bile Duct Ligated Rats", Hepatology, 2007, pp. 1517-1526.
Notification of Transmittal of the International Search Report and The Written Opinion of the International Searching Authority dated Sep. 27, 2017, 11 pages.

* cited by examiner

*Primary Examiner* — Pancham Bakshi
(74) *Attorney, Agent, or Firm* — Rothwell, Figg, Ernst & Manbeck, P.C.

(57) ABSTRACT

A method of treating or preventing type C Hepatic Encephalopathy in a human patient diagnosed with cirrhosis by administering a composition containing at least 200 mg biotin to the human patient daily.

20 Claims, 14 Drawing Sheets

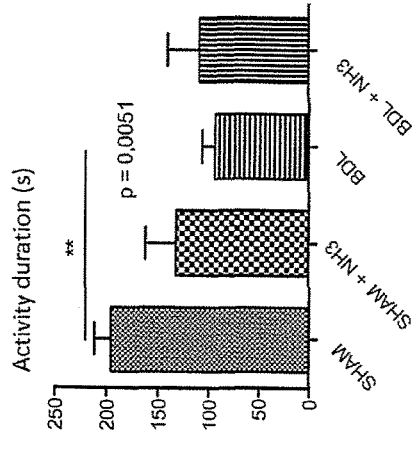
Fig. 2A
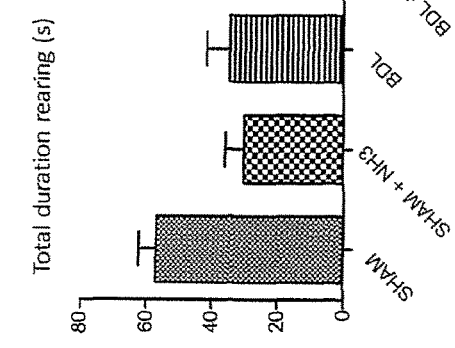
Fig. 2B
Fig. 2C
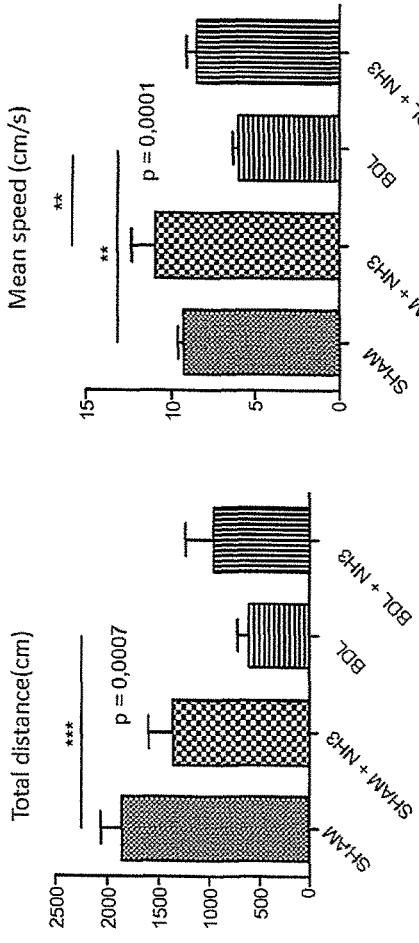
Fig. 2D
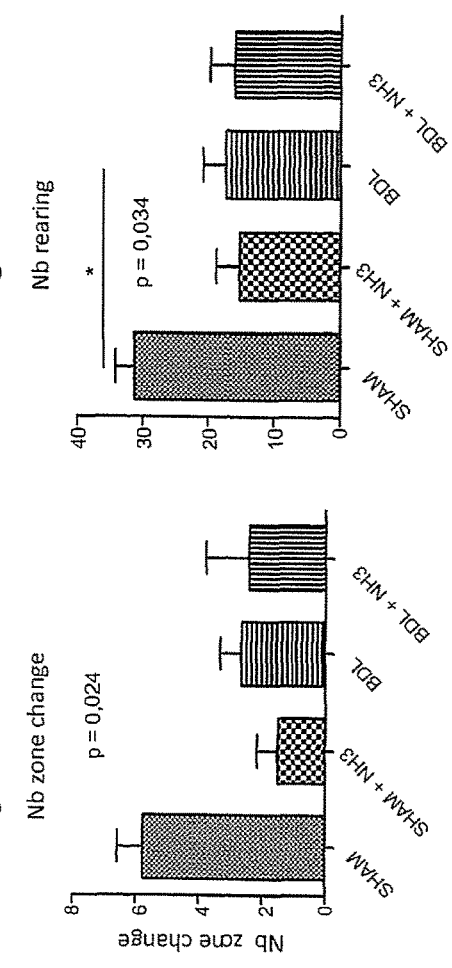
Fig. 2E
Fig. 2F

METHOD FOR TREATING HEPATIC ENCEPHALOPATHY

This application is a continuation of U.S. Ser. No. 15/935,695 filed Mar. 26, 2018, which is a continuation of International Application Number PCT/EP2017/069194, filed Jul. 28, 2017, which claims the benefit of European Patent Application No. 16305989.2, filed Jul. 29, 2016.

The invention relates to the treatment of hepatic encephalopathy.

Hepatic encephalopathy (HE), also known as portosystemic encephalopathy, is a severe complication of acute or chronic liver failure.

Patients suffer from various neurologic and neuropsychiatric abnormalities (asterixis, confusion, altered level of consciousness, coma as a result of liver failure). During cirrhosis, hepatic encephalopathy negatively impacts patient survival. About 30% of patients dying of end-stage liver disease experience significant encephalopathy, approaching coma.

Consequently, the economic burden of hepatic encephalopathy is substantial, as it is the second most common reason for hospitalization of cirrhotic patients in the United States.

Hepatic encephalopathies can be subdivided in type A, B and C depending on the underlying cause.

Type A (=acute) describes hepatic encephalopathy associated with acute liver failure, typically associated with cerebral oedema. Acute liver failure is a rapid deterioration (within days and weeks) of liver function in a person who had no pre-existing liver disease. Acute liver failure is commonly caused by paracetamol (acetaminophen) overdose, idiosyncratic reaction to medication (e.g. tetracycline, troglitazone), autoimmune causes, viral hepatitis (hepatitis A or B), acute fatty liver of pregnancy, or can be idiopathic.

Type B (=bypass) is caused by portal-systemic shunting without associated intrinsic liver disease. The blood thus by-passes the liver, which therefore cannot metabolize and clear blood substances which can be toxic like ammonium. Type B usually occurs as a result of congenital abnormalities and/or as a result of an invasive procedure or trauma.

Type C (=cirrhosis) occurs in patients with cirrhosis. Cirrhosis is a late stage of chronic liver disease when scarring (fibrosis) develops. The major causes of cirrhosis are:
- chronic alcoholism
- viral infections caused by chronic viral hepatitis (types B, C and D)
- metabolic diseases such as NASH (Non Alcoholic Steato Hepatitis)
- alpha-1-antitrypsin deficiency, galactosemia and glycogen storage disorders
- inherited diseases such as Wilson disease and hemochromatosis
- biliary cirrhosis resulting from diseases such as primary biliary cholangitis (PBC) and primary sclerosing cholangitis (PSC)
- toxic hepatitis caused by severe reactions to prescribed drugs or prolonged exposure to environmental toxins
- repeated bouts of heart failure with liver congestion.

Type-C HE can be subdivided in episodic (return to normal neural state between episodes), persistent (no return to normal neural state) and minimal encephalopathy (Bajaj, Aliment Pharmacol Ther. 2010 Mar; 31(5):537-47).

Minimal encephalopathy is an encephalopathy that does not lead to clinically overt cognitive dysfunction, but can be evidenced using neuropsychological tests, and has been demonstrated to impair quality of life and to increase the risk of involvement in road traffic accidents.

Minimal HE may affect 30-70% of patients with cirrrhosis; overt HE (either episodic or persistent) is observed in 30-45% of patients with cirrhosis during their lifetime. It is to be noted that HE, even minimal, is an independant risk of mortality.

The physiopathology of hepatic encephalopathy is still debated but many hypothesis are studied. Ammonia may have a central key role, together with systemic inflammation and changes in specific carriers on the blood-brain barrier. Hepatic encephalopathy could be a consequence of accumulation in the bloodstream of toxic substances, in particular ammonia, that are normally cleared by the liver. Ammonemia is not sufficient to induce HE. It is hypothetized that a combination of both increased blood ammonia and inflammation is necessary for HE to occur, in particular by a modification of the blood-brain barrier leading to intracerebral accumulation of toxic substances and modulation of neurotransmission.

Treatments of Hepatic Encephalopathy

Most specific current therapies are designed to decrease intestinal ammonia production and the resulting hyperammonemia.

During acute hepatic encephalopathy, lactulose (beta-galactosidofructose) or lactilol (beta-galactosidosorbitol) are given to patients to accelerate the transit and to inhibit intestinal ammonia production. These are nonabsorbable disaccharides that are degraded by intestinal bacteria to lactic acid and other organic acids. Lactulose is administered to patients at a dose of 30 mL orally, daily or twice daily, and the dose may be increased, or reduced, depending on the tolerance or adverse effect observed in the patients.

Higher doses of lactulose (60 mL every eight hours) may be administered to patients with severe hepatic encephalopathy. Lactulose is given after the first episode of hepatic encephalopathy to prevent recurrence.

Various antibiotics are also used, in order to decrease the ammoniagenic bacterial load. Antibiotics are generally used if treatment with lactulose is not effective enough and in secondary prevention.

One can use neomycin, metronidazole, rifaximin, oral vancomycin, paromomycin, and oral quinolones. Rifaximin a nonabsorbable derivative of rifampin with a broad spectrum antibacterial activity. It can reduce endotoxemia, including hyperammonemia, by reducing the intestinal translocation of bacteria. Used in a number of trials, rifaximin effect was equivalent or superior to the compared agents with good tolerability. The recommended posology is 550 mg twice a day. Recently, therapies used for the treatment of inborn errors of urea metabolism begin to be used in patients with hepathic encephalopathy, but are not yet formally recommended. These include:

A stable salt of 2 constituent amino acids, L-ornithine and L-aspartate (LOLA), can also be used to increase ammonia clearance. It may be combined with lactulose and/or rifaximin.

Sodium benzoate, sodium phenylbutyrate, sodium phenylacetate, and glycerol phenylbutyrate may also be used for the treatment of hepatic encephalopathy. The oral doses of sodium benzoate are about 5 g twice a day, although lower doses (2.5 g three times a week) may also help patients recover from symptoms of hepatic encephalopathy. Glycerol phenylbutyrate may be used at an oral dose of 6 ml twice-daily.

Nutritional intervention is necessary in case of malnutrition or insufficient dietary intake. Eating vegetables proteins rather than proteins derived from red meat, and chicken and fish proteins may be favourable. It is also advised to supplement the diet with branched-chain amino acids. Zinc administration can also be used, with the potential to improve hyperammonemia, with zinc sulfate and zinc acetate that can be administered at a dose of 600 mg orally every day. L-carnitine is also used to improve hepatic encephalopathy symptoms, in particular in patients with cirrhosis.

WO 2011/124571 describes the use of biotin at a high dose (in the range of 100 to 600 mg/day) for the treatment of visual impairments, in particular related to optic atrophy. It should be noted that the visual impairments actually described in this application are symptoms related to a particular leukoencephalopathy, i.e. an involvement of the white matter of the brain. This document neither describes nor suggests that biotin could be used for the treatment of HE.

WO 2014/016003 describes the use of biotin at a high dose (of the order of 100 to 600 mg/day) for the treatment of multiple sclerosis (MS), stroke and X-linked adrenoleukodystrophy (X-ALD), in particular adrenomyeloneuropathy (AMN). WO 2014/177286 provides evidence that biotin is useful for treatment of AMN.

WO2016151132 provides evidence that biotin is useful for treating amyotrophic lateral sclerosis (ALS).

Nagamine et al (J Gastroenterol. 1995 Jun; 30(3):351-5; and Nihon Shokakibyo Gakkai Zasshi. 1989 Jul; 86(7): 1519-24) and in JPH01226814A have induced acute hyperammonemia in rats by administering urease or ammonium acetate. In another model, acute liver failure was induced by injecting a single high dose of $CCl_4$. The authors observed an ability of biotin to decrease the serum ammonium level in this animal acute liver failure model. The amount of biotin when administered was not controlled when given orally and was 0.5 mg/kg BW (body weight) when a single dosed was injected intraperitoneally (Nagamine, 1989). In Nagamine (1995), the dose of biotin (provided as a single intraperitoneal shoot) is also very low.

In JPH01226814A, the biotin is provided as a single intraperitoneal shoot of 1 mg of biotin. Results are reported for human, with doses used therein in the range of a few mg (about 5-10 mg) per day. The results reported for the patients are, however, not conclusive. Indeed, there is a high natural variability of the general state and of the ammonia level in the serum of patients with HE. Tables 7 and 8 only report data obtained during 10 days, without any control or information about other treatments that the patients received. From patient 2, it can be seen that there is a high variability in the ammonia level (rising and decreasing) for the first 5 days, even tough this patient did not receive any biotin during this timespan. It is also true for patient 3, where ammonia level had well decreased between days 48 and 96 although no biotin had been administered to the patient in this timespan. There is thus no possibility to reach a conclusion on the actual role of biotin on ammonia levels and for controlling HE in these patients.

It is further to be noted that despite the results reported therein more than 20 years ago, no drug based on biotin was developed or proposed to the market to treat or prevent hepatic encephalopathy.

In particular, a review by Bajaj (2010, Aliment Pharmacol Ther 31, 537-547) does not mention biotin as a product that is or can be used for the treatment of type C hepatic encephalopathy.

In the context of the present invention, it is proposed to use biotin, at a much higher dose, in order to improve the condition of patients suffering from hepatic encephalopathy.

The fact that biotin at a high dose (a higher dose than the one presented in the prior art) can be useful for hepatic encephalopathy treatment and could ultimately limit the evolution of the disease, and even revert some symptoms thereof is particularly novel and surprising.

The invention therefore relates to biotin for use thereof in the treatment or prevention of hepatic encephalopathy, wherein the biotin is very preferably used a a high dose, i.e. at least 100 mg per day. It is preferably used at a daily dose higher than 100 mg.

Also subjects of the invention are compositions containing biotin for the use thereof in the treatment of hepatic encephalopathy, and also the use of biotin for the production or manufacture of a drug intended for the treatment of hepatic encephalopathy. In particular, the drug shall contain more than 20 mg, more preferably more than 40 mg, more preferably more than 50 mg, more preferably more than 70 mg, more preferably about or exactly 100 mg of biotin, in particular when used by oral administration.

The teachings of the invention thus make it possible to implement treatment methods comprising the administration of biotin to patients suffering from hepatic encephalopathy. The invention thus also relates to a method for treating a patient suffering from hepatic encephalopathy, comprising the step of administering biotin to said patient. Examples of dosage of biotin, and treatment regimen are disclosed below.

Biotin can be used alone or in combination with another compound used for treating hepatic encephalopathy (or symptoms thereof).

The invention therefore covers a composition containing biotin and also another medicament, as listed above, against hepatic encephalopathy, for simultaneous, separate or sequential (spread out over time) use in the treatment of a hepatic encephalopathy.

The invention also describes and relates to a method of treating a patient suffering from hepatic encephalopathy, comprising the steps of providing biotin to said patient, and optionally (but preferably) another drug useful for providing relief to said patients with regards to the symptoms of hepatic encephalopathy.

Biotin can, in particular, be used to improve cognitive and psychomotor processing speed, memory and motor control and coordination.

Treatment with biotin can also lead to increase of the weight of the patient.

The biotin is preferably used for treating type C hepatic encephalopathy, whether persistent, episodic or minimal. However, biotin may be used in patient with type A or type B hepatic encephalopathy to decrease the symptoms before the situation comes back to normal. Administration of biotin to type A patients would allow these patients to wait for a longer time before receiving a liver graft and/or to be in a better condition when receiving it.

Biotin can also be used for preventing episodes of hepatic encephalopathy. In particular such prevention is useful in patients with diagnosed cirrhosis, whether they have already presented an episode of HE (i.e. whether they have episodic or persistent HE) or whether they have not been diagnosed with HE (they have not presented any episode of HE symptoms, or no clinical sign of HE), and thus have minimal HE or no HE at all.

Biotin at a high dose is particularly interesting to prevent secondary episodes of HE, in patients that have already presented an episode of HE.

For treatment of the above disease, or preparation of a drug intended for the treatment of the above disease, biotin may be used as follows.

The biotin is preferentially administered at a therapeutically effective amount, which is generally a high dose, i.e. at a dose of at least or about or exactly 100 mg per day. Even if a maximum dose is not really envisaged, the latter should not generally exceed 500 mg, 600 mg or 700 mg per day. This makes it possible to observe improvement in the condition of the patient, and/or stop or decrease of the worsening of the condition of the patient.

In that way, the physician may determine the dose according to the weight of the patient. In particular, a dose at least equal to 1 mg/kg/day, preferably 3 mg/kg/day, preferably 5 mg/kg/day, or at least equal to 7.5 mg/kg/day, or even around 10 mg/kg/day, is administered to the patient.

Between 100 and 700 mg of biotin per day are thus preferably administered to the patients, generally between 100 and 500 mg per day, or between 100 and 600 mg per day, more preferably between 100 and 300 mg per day, generally around or exactly 300 mg per day. One can thus administered at least or about or exactly 100 mg per day, or at least or about or exactly 150 mg per day, or even at least or about or exactly 200 or at least or about or exactly 250 mg per day, or at least or about or exactly 300 mg per day.

In one particular embodiment which is preferred (in particular for problems of ease of use by the patient), the biotin is in a form suitable for oral administration. This therefore involves a composition for oral administration, which will contain at least or about or exactly 20 mg, preferably at least or about or exactly 40 mg of biotin, or even at least or about or exactly 50 mg, at least or about or exactly 75 mg, at least or about or exactly 100 mg, at least or about or exactly 150 mg or at least or about or exactly 250 mg of biotin, or at least or about or exactly 300 mg of biotin. This composition is preferentially for pharmaceutical use, and is therefore a medicine. It is understood that each unit dose of this composition contains at least or about or exactly 20 mg, preferably at least or about or exactly 40 mg, or even at least or about or exactly 50 mg, at least or about or exactly 100 mg, at least or about or exactly 150 mg or at least or about or exactly 250 mg of biotin or about or exactly 300 mg of biotin, as active ingredient.

The total dose of biotin may be administered once a day, or through multiple intakes. In particular, biotin may be taken through two or three intakes a day. It is preferred when biotin is taken around meal times, and when the amount of biotin is substantially the same for each intake.

It is to be noted that the diseases herein described are chronic diseases, with worsening over time. It is thus preferable that treatment with biotin is performed in the long run, in order to be the most effective, to prevent the occurrence of new HE episodes and to stabilize any improvement that it will bring. Consequently, it is preferred when said treatment with biotin has a duration of at least 3 months. It is even preferred when said treatment with biotin has a duration of at least 6 months.

As indicated, such treatment may be extended as long as possible in order to prevent the occurrence of new HE episodes, increase the improvement that could bring biotin, and stabilize the therapeutic effects. In particular, said treatment with biotin has a duration of at least one year. There is no envisioned end for the treatment and it is expected that the patient will take biotin as long as it is needed and will stabilize or improve the condition of the patient.

In one particular embodiment, this composition for oral administration contains biotin as sole active ingredient, and also excipients, without any other active ingredient.

An excipient should be understood to mean any compound being part of the formulation which is intended to act as a simple support, i.e. which is not intended to have a biological activity.

This composition can be in any form known in the art. In particular, it is in the form of gel capsules, tablets (optionally film-coated), pills or lozenges. In another embodiment, it is in the form of a syrup. Said syrup contains an amount such that it contains at least or about or exactly 20 mg, preferably at least or about or exactly 40 mg, or even at least or about or exactly 50 mg, at least or about or exactly 75 mg or at least or about or exactly 100 mg of biotin per unit dose. The concentration of biotin in this syrup depends on the unit dose that it is desired to give to the patient.

Excipients which can be used by those skilled in the art are well known in the art. Talc (E553b), microcrystalline cellulose, lactose, mannose, starch (in particular corn starch), magnesium stearate (E572) and stearic acid (E570) can thus be chosen. This list is not exhaustive.

When this composition is prepared in the form of gel capsules, a preferred excipient is microcrystalline cellulose.

When the composition is in the form of a film-coated tablet, said film-coating may be formed from any substance known in the art, such as hypromellose (E464), ethylcellulose, macrogol, talc (E553b) titanium dioxide (E171) or iron oxide (E172).

The active ingredient may also be colored (by any acceptable coloring, such as cochineal), thereby making it possible to verify that the biotin is well dispersed in the excipient.

A slow release (or slow sustained) form may also be envisaged given the fact that plasma half life of biotin is short (about 2 hours).

Said slow release compositions are known in the art and described in particular in WO 2011/077239. In particular, said slow release compositions may comprise a slow release matrix comprising biotin alone or with one or more active ingredient(s).

In a specific embodiment, the slow release composition comprises a matrix allowing immediate release, wherein said matrix comprises biotin alone or with one or more other active ingredient(s) and the slow release is achieved by a release modifying matrix or coating.

Thus, the slow release composition may provide immediate release and differed (slow) release of biotin.

In a specific embodiment slow release may be achieved through an osmotically driven release system.

In another embodiment, the slow release composition comprises a core comprising biotin, optionally one or more active ingredient(s), and optionally pharmaceutical excipient(s) and one or more outer layers, wherein the outer layers comprises one or more slow release agent(s).

In another aspect, the biotin may be in the form which allows administration by injection: this then involves an injectable composition containing at least or about or exactly 20 mg, preferably at least or about or exactly 40 mg, or even at least or about or exactly 50 mg, at least or about or exactly 75 mg, at least or about or exactly 100 mg, at least or about or exactly 150 mg or at least or about or exactly 250 mg of biotin per unit dose.

This injectable composition may be in the form of a vial containing the biotin, and also acceptable excipients. The concentration of biotin is adjusted according to the envisaged volume of the vial. Certain excipients which improve biotin solubility can be used.

The excipients that can be used for the production of injectable compositions are well known in the art. Mention may in particular be made of sodium dihydrogen phosphate, sodium bicarbonate (E550i), methyl para-hydroxybenzoate (E218) and propyl para-hydroxybenzoate (E216), which can be used together in proportions that those skilled in the art are capable of determining. The water used is water for injection. The injection is preferably carried out intramuscularly. It can also be carried out intravenously.

DESCRIPTION OF THE FIGURES

FIG. 2A-F: 6 minutes comportmental analysis of control and BDL rats without or with a water enriched in NH3. FIG. 2A. Total distance; FIG. 2B. mean speed; FIG. 2C. activity duration (time during which the animal is active rather than passive); FIG. 2D. number of zone changes; FIG. 2E. number of rearing; FIG. 2F. total duration of rearing.

FIG. 5A. Total distance; FIG. 5B. mean speed; FIG. 5C. activity duration (time during which the animal is active rather than passive); FIG. 5D. number of zone changes; FIG. 5E. number of rearing; FIG. 5F. total duration of rearing.

FIG. 7A. Total distance; FIG. 7B. mean speed; FIG. 7C. activity duration (time during which the animal is active rather than passive); FIG. 7D. number of zone changes; FIG. 7E. number of rearing.

FIG. 8A. Total distance; FIG. 8B. mean speed; FIG. 8C. activity duration (time during which the animal is active rather than passive); FIG. 8D. number of zone changes; FIG. 8E. number of rearing.

FIG. 9A. control and BDL rats without or with water enriched in NH3. FIG. 9B. control (oil) and rats injected with $CCl_4$ rats without or with a diet enriched in NH3.

FIG. 10A. control and BDL rats without or with a diet enriched in biotin (300 mg/kg of food). FIG. 10B. control (oil) and rats injected with $CCl_4$ rats without or with a diet enriched in biotin (50 mg/kg of food).

EXAMPLES

Example 1

Figure 1:
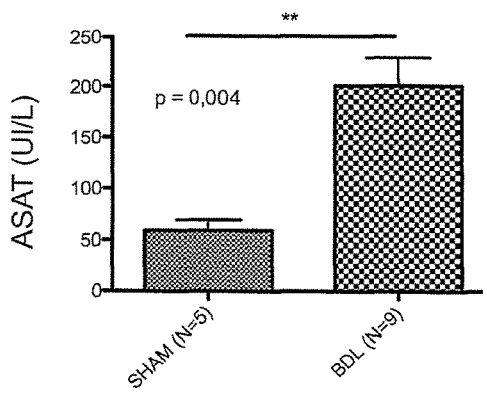
FIG. 1A-D: levels of ASAT (FIG. 1A), ALAT (FIG. 1B), bilirubin (FIG. 1C) and albumin (FIG. 1D) in the serum of control (sham) or bile duct ligated (BDL) rats.
Figure 1:
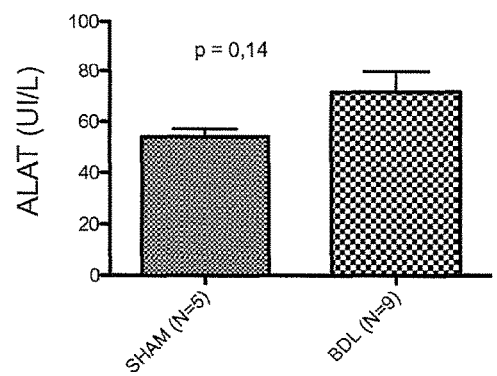
Figure 1C:
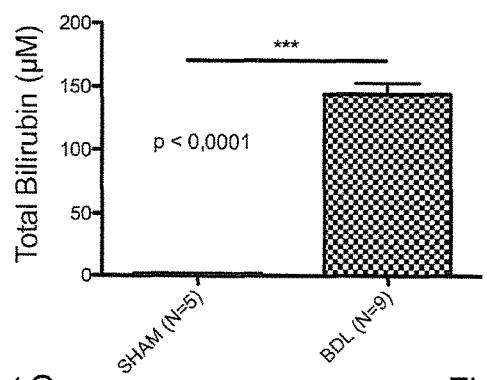
Figure 1D:
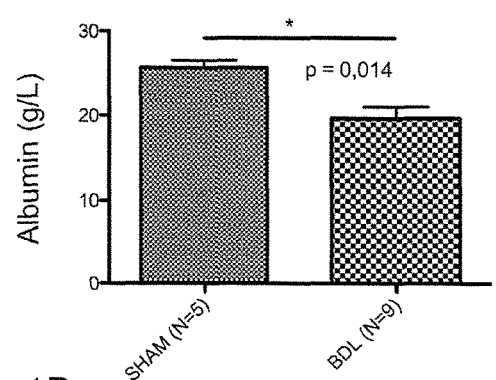

Study in the Rat Bile Duct Ligation Model Plus Hyperammonemic (NH3-Enriched) Water Rats with bile duct ligation (BDL) is a model of cholestatic liver injury with associated oxidative stress and fibrogenesis.

These rats develop progressive hepatic injury with the onset of fibrosis within 2 weeks and the development of biliary cirrhosis within 4-6 weeks.

When given hyperammonemic supplements, more bile duct ligated rats develop encephalopathy.

The effect of biotin is evaluated in bile duct ligated rats treated with hyperammonemic water regarding clinical efficacy in terms of orientation in open-field and body weight gain.

"Clinical" Evaluation:
  4 groups of 5 rats: sham-operated rats treated with either 1) control diet and control water; 2) control diet and hyperammonemic (NH3-enriched) water; 3) biotin-supplemented diet and control water; and 4) biotin-supplemented diet and hyperammonemic water.
  4 groups of 10 rats: bile duct-ligated rats treated with either 1) control diet and water; 2) control diet and hyperammonemic water; 3) biotin-supplemented diet and control water; and 4) biotin-supplemented diet and hyperammonemic water.
  The dose of biotin used is 30 mg/kgBW/day which is equivalent to a human dose of 300 mg/day.
  Biotin is delivered mixed in dry food
  "Clinical" examination:
    Weight
    Open-field (orientation)
  Treatment start: at day 3 post-surgery
  Treatment is continued for 6 weeks, when rats are cirrhotic.
  Blood-brain barrier permeability is evaluated at the end of the study.

This experiment makes it possible to evaluate the effect of high-dose biotin treatment in terms of clinical improvement, blood-brain barrier reduction and metabolic normalization, in a model of chronic HE.

Example 2

Another Model of Hepatic Encephalopathy in Rats is the Model of Liver Fibrosis Induced $CCl_4$ plus hyperammonemic water Rats administered with $CCl_4$ have hepatotoxicity mediated by free radical production.

These rats develop progressive hepatic injury with development of cirrhosis within 8 weeks.

When given hyperammonemic supplements, more $CCl_4$-treated rats develop encephalopathy.

The same clinical protocol as described in Example 1 is applied to these animals.

Example 3

Detailed Material and Methods

Animals

Adult male Wistar rats (weight 175-200 g at the initiation of the surgical procedure) were obtained from the Janvier labs (Le Gesnest-Saint-Isle) and were used for the whole experiments.

Bile Duct Ligation

Bile duct ligation (BDL) was used as a biliary cirrhosis model. All rats oh this group were operated on. They were randomly separated in two groups : BDL or simple laparotomy (SHAM, control-group). The BDL procedure was conducted as described previously (Kountouras J, Prolonged bile duct obstruction: a new experimental model for cirrhosis in the rat; Br J Exp Pathol 1984) and as controlled in our lab. Surgery was done under total anesthesia with inhalated isofluran (Aerrane, Baxter Maurepas) 3% mixed with air. Analgesia was done by sub-cutaneous injection of buprenorphin 2% (Buprécare 0.3 mg/ml, Axience) immediately before and after surgery.

Animals were examined twice a week and weighted weekly. All animals were maintained for 6 weeks following surgery.

$CCl_4$

In order to obtain a control of the results, another cirrhosis model was used, consisting in a chronic poisoning by carbon tetrachloride ($CCl_4$); Wistar rats received $CCl_4$ 1 ml/kg body weight twice weekly for 8 weeks in mineral oil. Controls received mineral oil without $CCl_4$. Treatments were administered intragastrically by gavage using a polyethylene catheter, without sedation.

The dose of $CCl_4$ used in this experiment is below the dose used in Nagamine, which is more a model of acute liver injury (type A HE).

In the present model, use of a lower dose over a longer time makes it possible to better mimic pregressive liver injury and thus type C HE.

Hepatic Encephalopathy

An intervention was used (Wright et al, Hepatology 2007, Jun; 45(6):1517-26) with the aim to increase hepatic encephalopathy incidence and consisted of addition of high protein/ammoniagenic food supplements (NH3-enriched supplements) for 6 or 8 weeks (depending on the cirrhosis model). The NH3 treatment began 3 days after the surgery or $CCl_4$ procedure. It consisted of a tailor-made mixture mimicking the amino-acid composition of the hemoglobin molecule (4 g/kg/g; EF Rat Hyperammonemia AA mixture Crude protein 88.9%, SSNIFF) mixed with water. Rats were given 2 bottles, one with water only and one with the treatment.

The aim of this regimen was to produce chronic hyperammonemia.

Four groups of rats received this NH3-enriched treatment among BDL, SHAM, $CCl_4$ and oil.

Treatment Against Hepatic Encephalopathy

Rifaximin is an oral non-absorbable antibiotic validated in human to prevent recurrence of HE in association with lactulose. The exact mechanism of action is not well known but it supposed to decrease hyperammonemia and bacterial translocation because of its role on gut microbiota.

Thereby, it could play a role on the two main actors of HE, hyperammonemia and systemic inflammation.

Rifaximin (Sigma Aldrich) was mixed with water at the dose of 50 mg/kg/d and began 3 days after the surgery.

Four groups of rats received rifaximin (RFX): BDL, SHAM, BDL+RFX, SHAM+RFX.

Sodium benzoate, validated in genetic disorder of urea cycle, was also mixed with water at the dose of 200 mg/kg/d and began 3 days after the surgery.

Biotin was given mixed in animal food at a dose of 50 mg/kg or 300 mg/kg of food, corresponding to an ingested dose of 5 mg/kg of animal/day or 30 mg/kg of animal/day and a daily dose of 50 mg or 300 mg in human.

It it to be noted that biotin is provided to the animals prior to inducement of HE, as the animals only experience one HE episode and quickly die after the development of HE following Bile Duct Ligation. Therefore, in this animal model, biotin can't be provided after surgery to study the ability of biotin to prevent a second HE episode. Survival of the animals was not studied as the animals were sacrificed to study the Blood-Brain Barrier permeability.

Behavioral Test

To assess the hepatic encephalopathy, the Open Field Test (BioSeb) was used, a behavioral test validated in BDL rats to explore neurological impairments (Leke, Plos One 2012; 7(5)). The test was done the day of sacrifice, in standardized experimental conditions (hour, place, light, noise). Each rat was placed in a square 1 $m^2$ box and was free to explore the arena during 6 minutes. Two areas were defined in the square, center and periphery. Mobility parameters were registered by a three-dimensional camera. The data analyzed after 6 minutes of experiments were : total distance travelled (cm), time of mobility (s), speed (cm/s), number of zone changes, distance travelled in the center and periphery zone, time spent in the center and periphery zone, number of rearing, total duration of rearing.

Determination of BBB Permeability with the Use of Dextran Texas Red

The integrity of BBB was investigated by measuring the extravasation from intra-vascular compartment of dextran-Texas Red (Life Technologies) conjugated.

Six weeks after the surgery, all rats were anesthetized with inhalated isofluran 3%. 0.75 ml of fluorochrome was injected in the femoral vein (Texas Red 10 kDa 10 mg/ml) and circulated during 6 minutes. Then, we took a blood sample (2 ml) in the inferior vena cava by a median laparotomy. To remove the intravascular localized dye, we did a large thoracotomy to perfuse 300 ml of cold PBS (40 ml/min with a peristaltic pump) through the left cardiac ventricle.

After decapitation, the brain was rapidly removed and the olfactory bulbs and brain stem eliminated with the cerebellum.

After grinding the right hemisphere by vigorously shaking and centrifugation, the amount of fluorescent dextran (µg/g) in supernatants was measured by fluorimetry (Tecan Infinite M200) at 620 nm upon excitation at 588 nm. The content of dye was valued by interpolation in standard curve.

Biochemical and Histological Analysis

The blood sample taken during the sacrifice was centrifuged and the plasma was used to determine the levels of hepatic transaminases, total and conjugated bilirubin and ammonia. Plasmatic cytokines (IL6, TNFa, IFNg) were determined by a multiplex commercial kit.

After the sacrifice, livers were extracted and weighted; then we did a biopsy of the organ to determine the fibrosis status, confirm cirrhosis by a Sirius red coloring after fixing in 10% formalin.

If the METAVIR score was not F4 for the BDL rats, these animals were excluded of the analysis.

Statistical Analysis

All data were presented as mean +/− standard derivation and analyzed with Prism (Graphpad, v5.0c). Differences between groups were compared by using a one-way analysis of variance (ANOVA). When the ANOVA identified significant between-group differences, Dunnett's test was used for integroup comparisons.

The difference was considered to be statistically significant if p was inferior to 0.05.

Example 4

Results

Figure 3A:
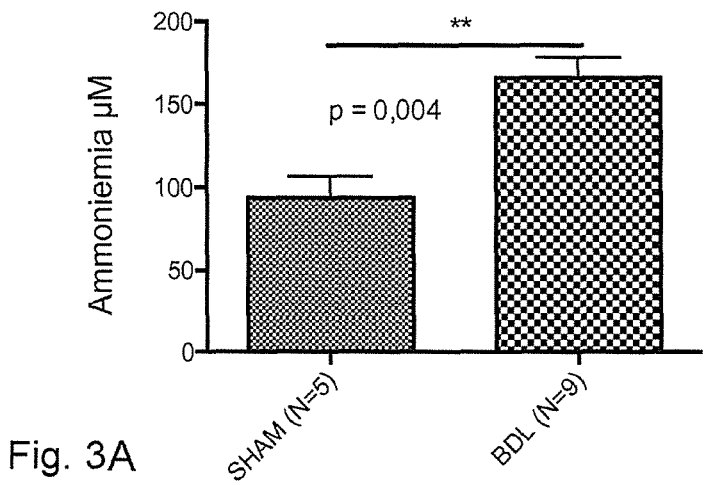
FIG. 3A-B: blood ammoniemia in control (sham) or BDL rats (FIG. 3A) or in rats injected with oil (control rats) or $CCl_4$ (FIG. 3B).
Figure 3B:
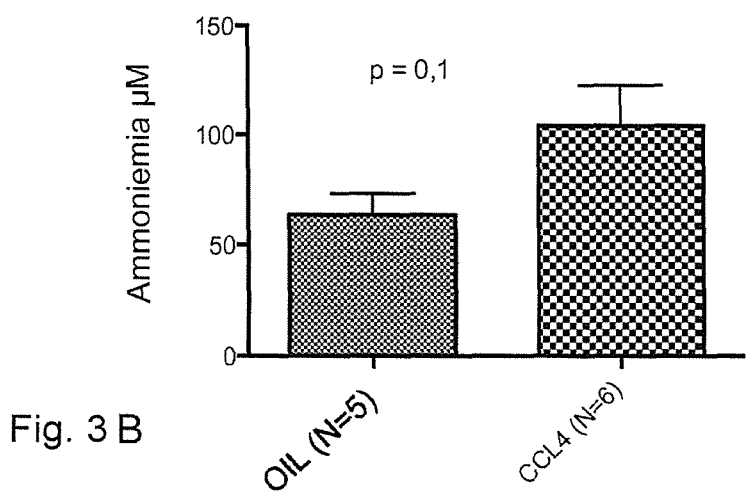
Figure 4:
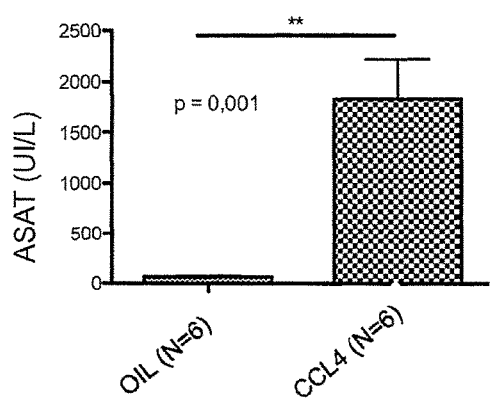
FIG. 4A-D: levels of ASAT (FIG. 4A), ALAT (FIG. 4B), bilirubin (FIG. 4C) and albumin (FIG. 4D) in the serum of control (oil) or rats injected with $CCl_4$.
Figure 4:
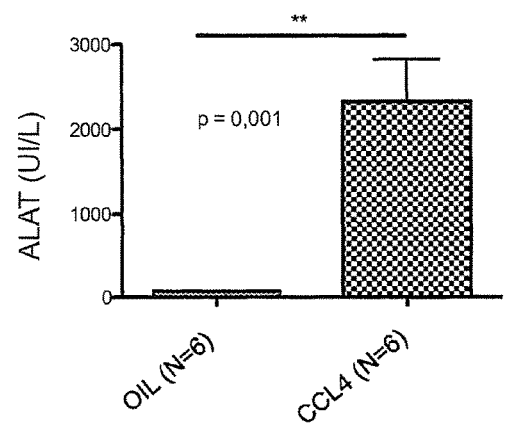
Figure 4:
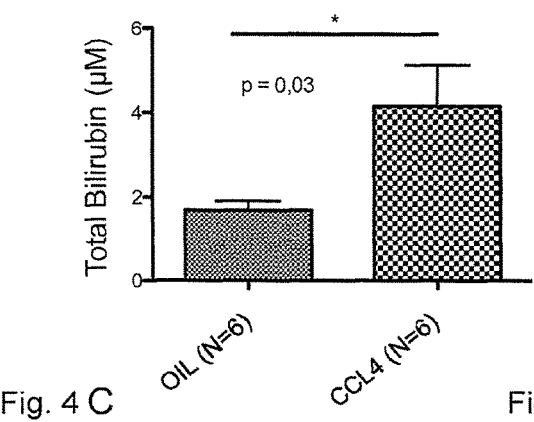
Figure 4:
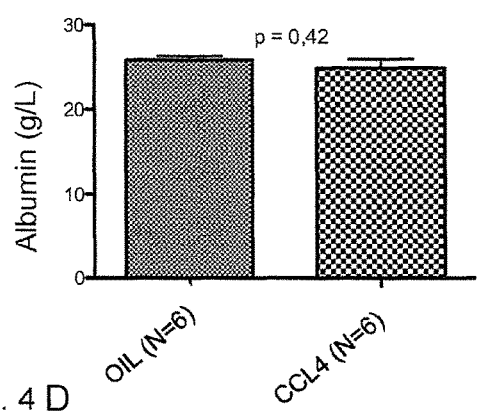
Figure 5A:
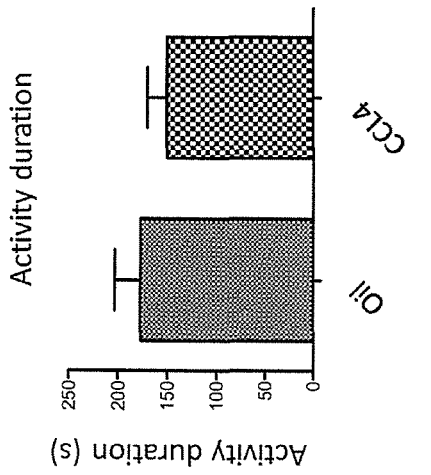
FIG. 5A-F: 6 minutes comportmental analysis of control (oil) and rats injected with $CCl_4$.
Figure 5B:
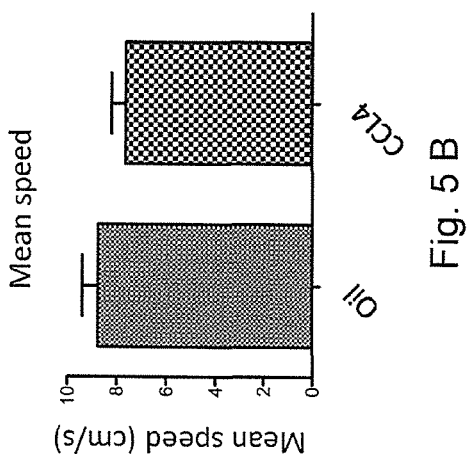
Figure 5C:
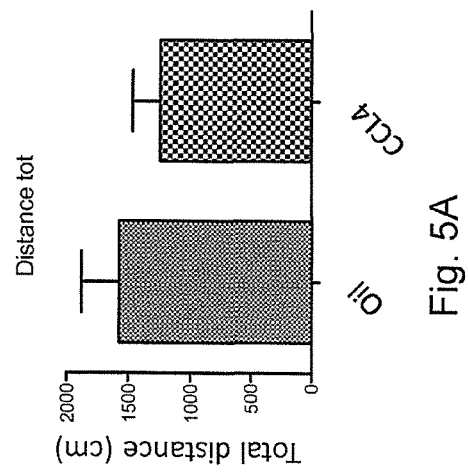
Figure 5D:
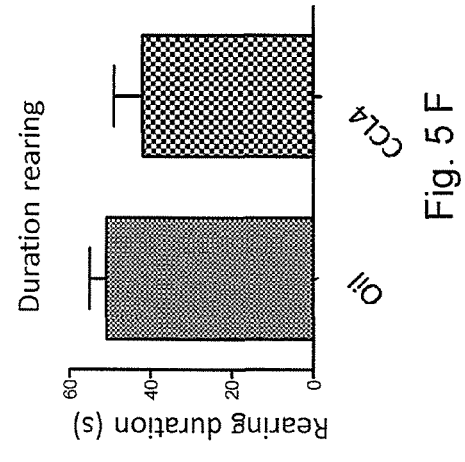
Figure 5E:
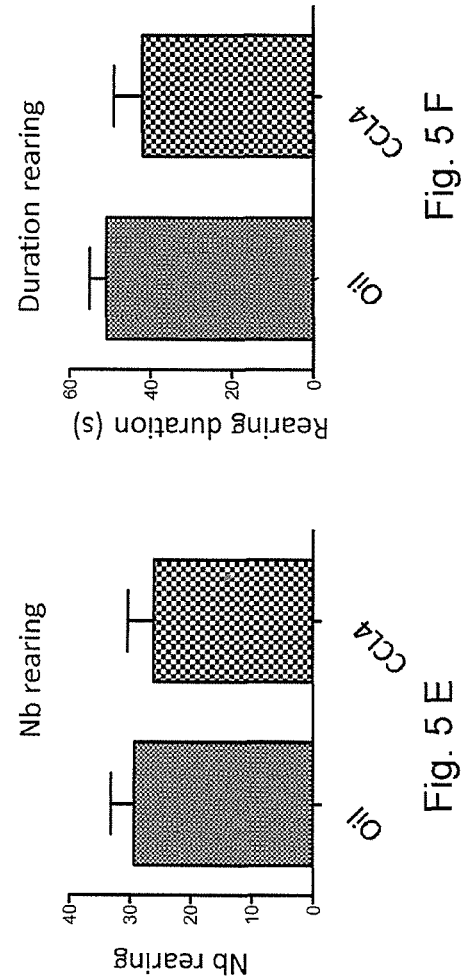
Figure 5F:
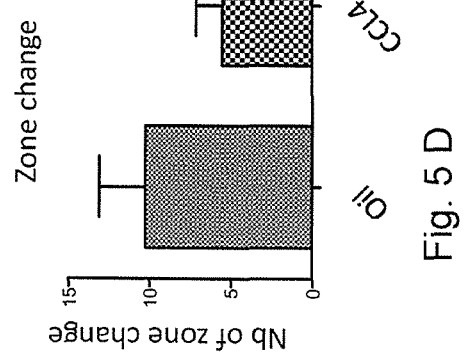

BDL and $CCl_4$ rat models both have cirrhosis. Extensive fibrosis and a destroyed architecture of the liver parenchyma can be observed, classified F4 with the METAVIR score. Consistently, the plasma hepatic markers are changed in the two models and differences between the two models reflects the origine of the liver disease. In BDL, the preponderant alteration is hyperbilirubinemia, whereas in $CCl_4$ it is transaminase (ASAT and ALAT) elevation (FIGS. 1A-D and 4A-D). Both BDL and $CCl_4$ rat models develop hyperammonemia (FIG. 3A-B).

The OpenField test shows that BDL rats develop neurological impairements: a significant shorter total distance travelled, a shorter duration of activity, a slower velocity, and less and shorter rearings, were observed, compared to Sham rats. These abnormalities were not found in $CCl_4$ rats. This suggests that BDL rats displayed HE in the OpenField test but not $CCl_4$ rats (FIGS. 2A-F and 5A-F).

Figure 6:
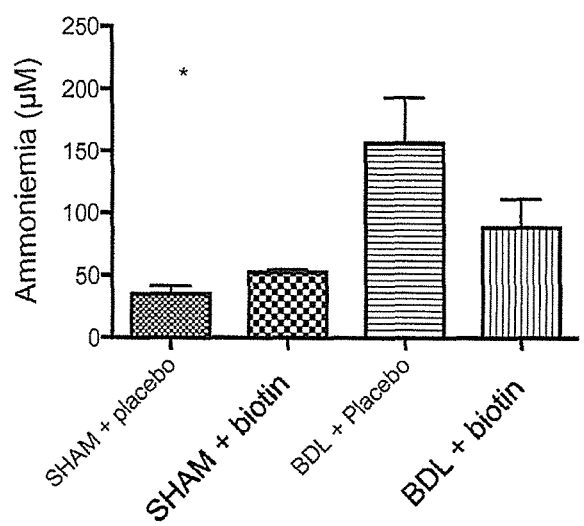
FIG. 6: blood ammoniemia in control or BDL rats fed with placebo or with biotin (300 mg/kg in food, corresponding to a daily dose of 30 mg/kg BW/day in rats or 300 mg/day in humans).
Figure 7B:
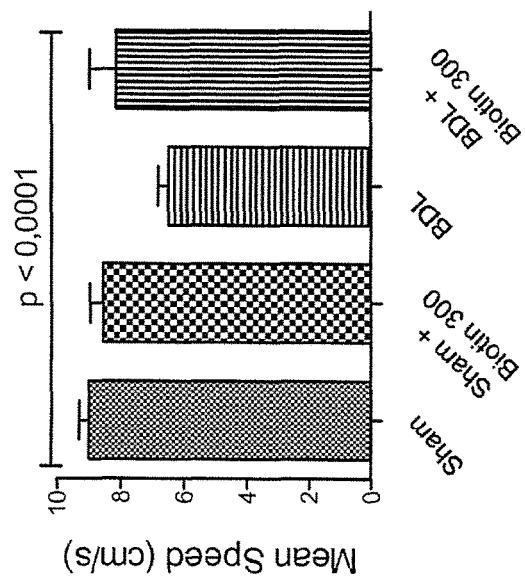
FIG. 7A-E: 6 minutes comportmental analysis of control (sham) or BDL rats, with a diet without or with biotin (dose corresponding to 300 mg in human).
Figure 7C:
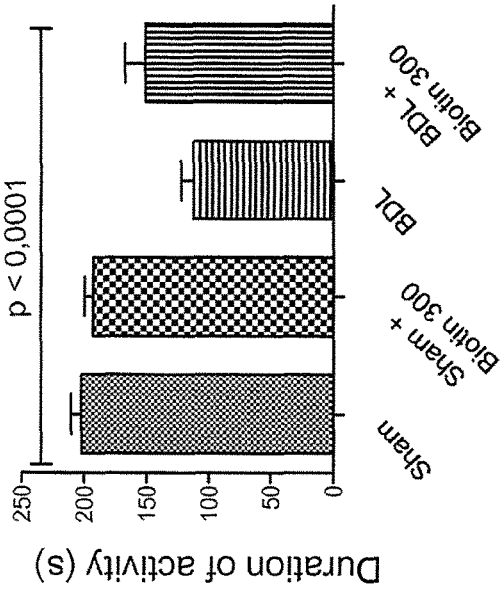
Figure 7A:
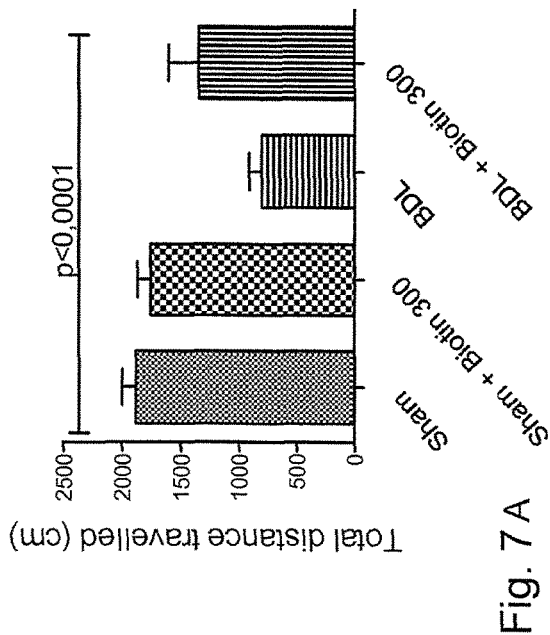
Figure 7:
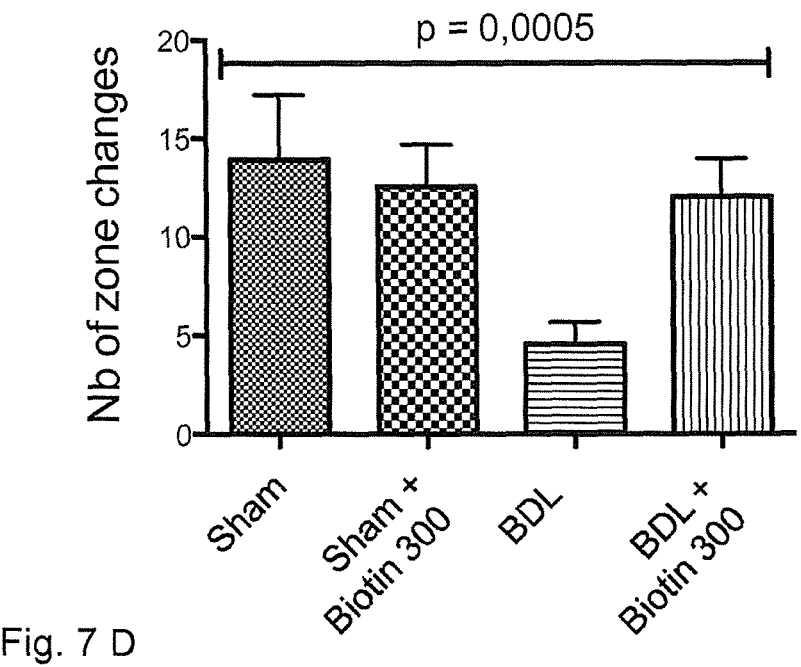
Figure 7:
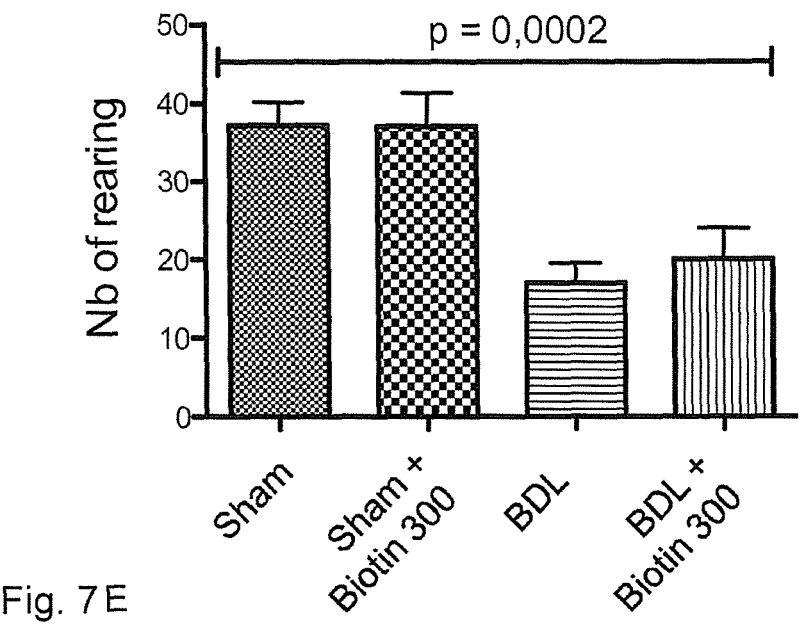
Figure 8:
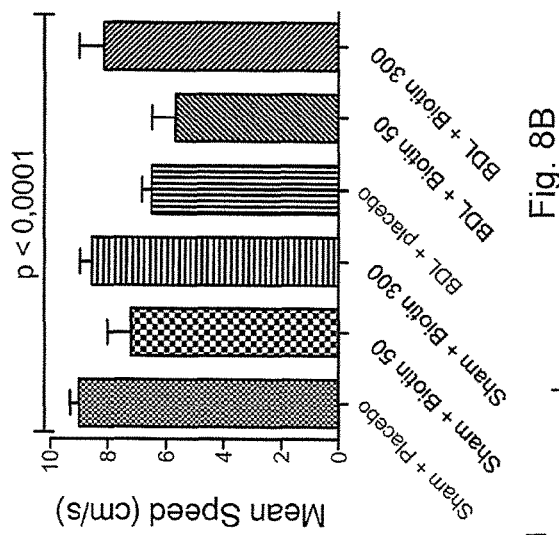
FIG. 8A-E: 6 minutes comportmental analysis of control and BDL rats without or with a diet enriched biotin (2 dosages corresponding to daily dose of 50 mg or 300 mg in human).
Figure 8:
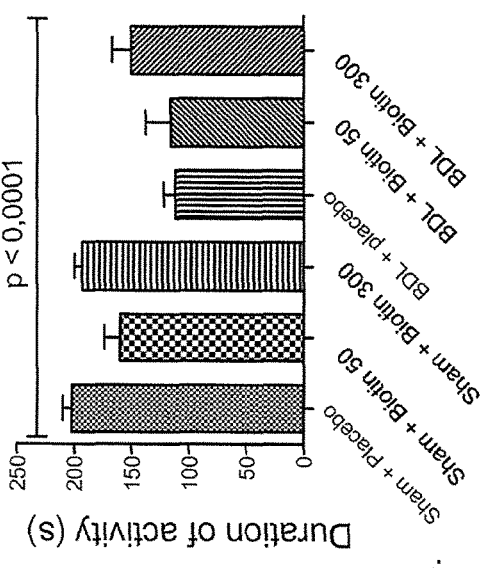
Figure 8:
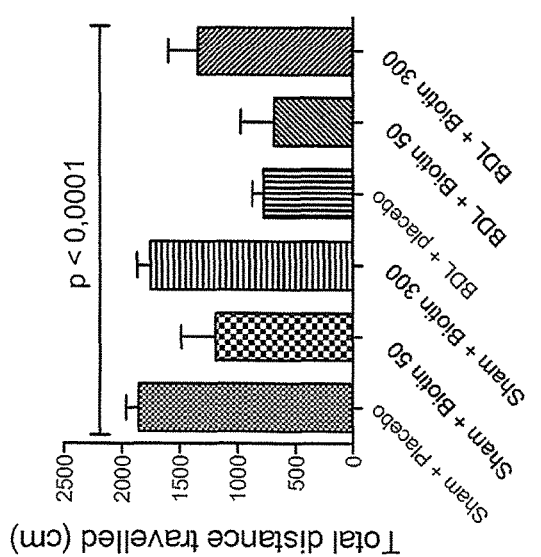
Figure 8:
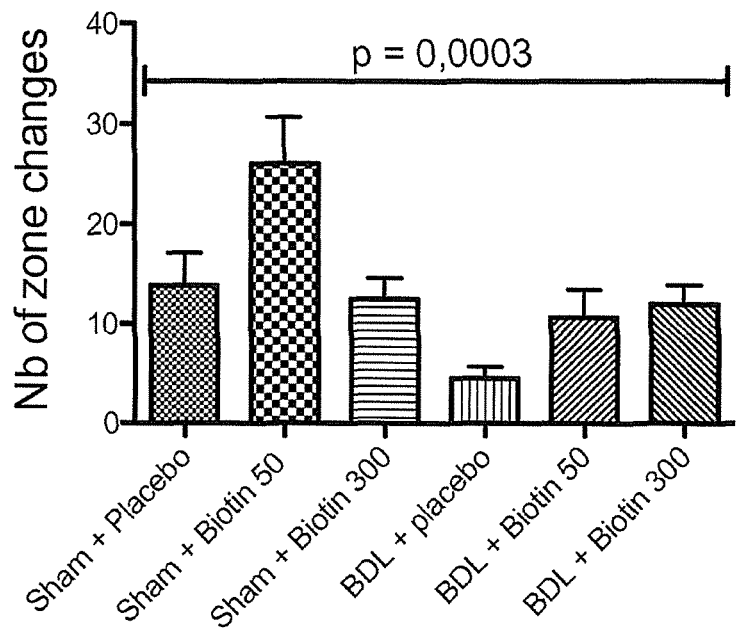
Figure 8E:
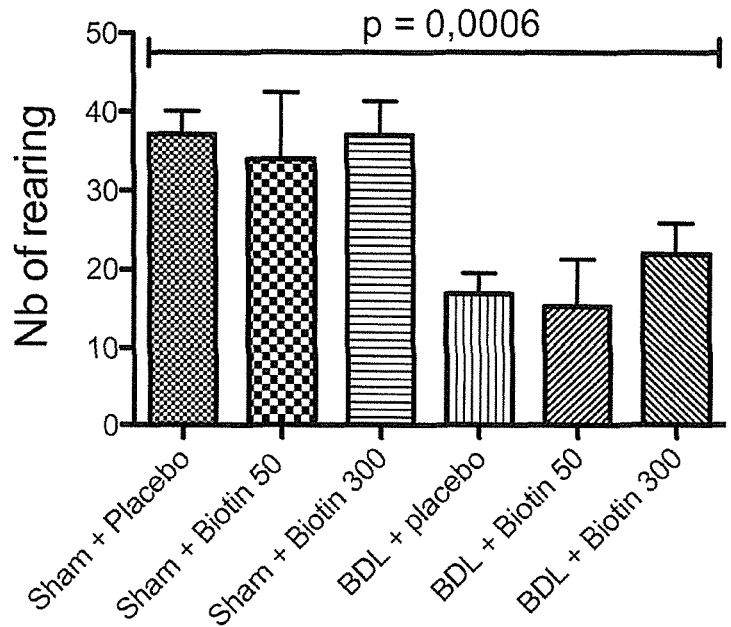
Figure 9:
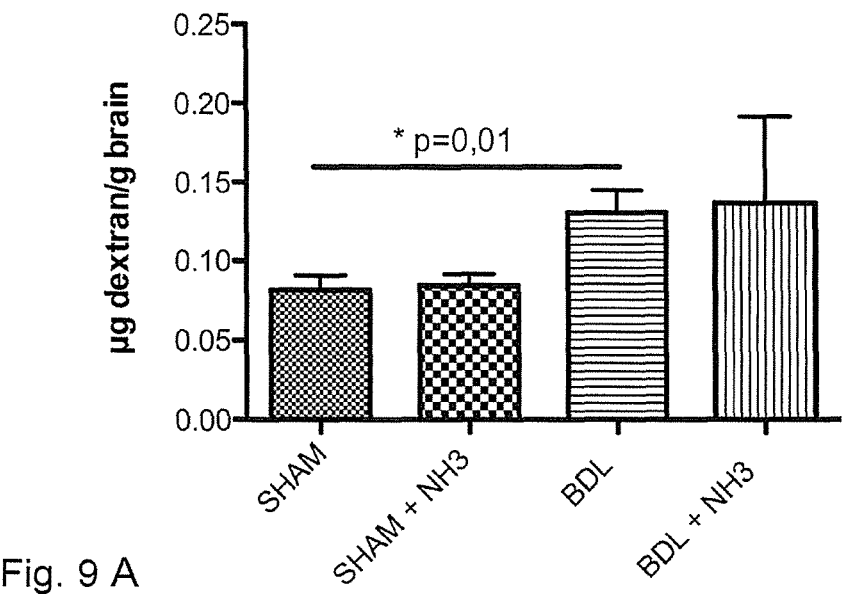
FIG. 9A-B: blood-brain barrier permeability observed by penetration into the CNS of Texas red coupled todextran.
Figure 9:
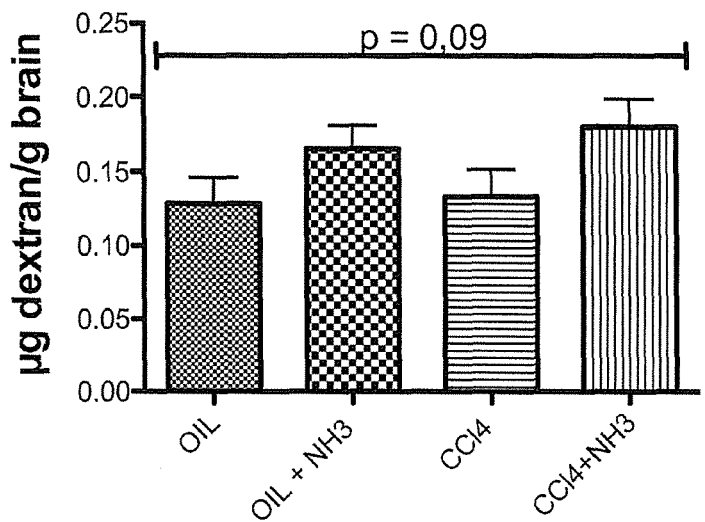
Figure 10A:
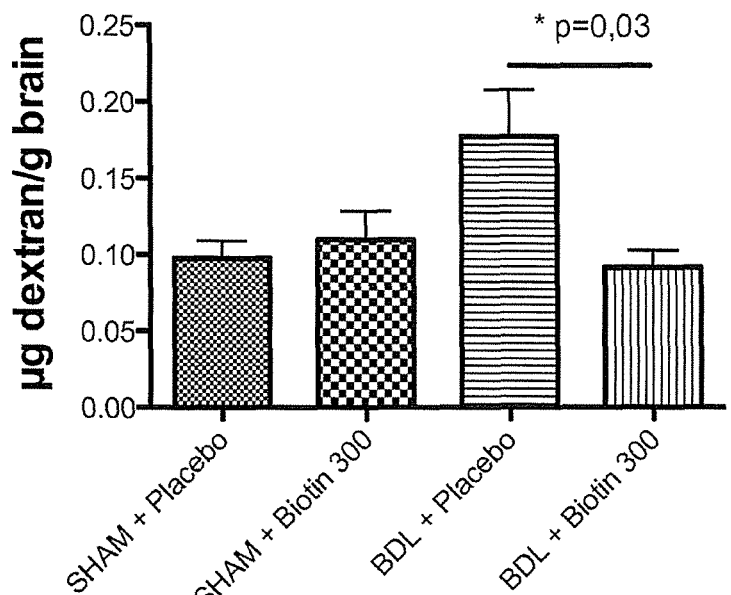
FIG. 10A-B: blood-brain barrier permeability observed by penetration into the CNS of Texas red coupled to dextran.
Figure 10B:
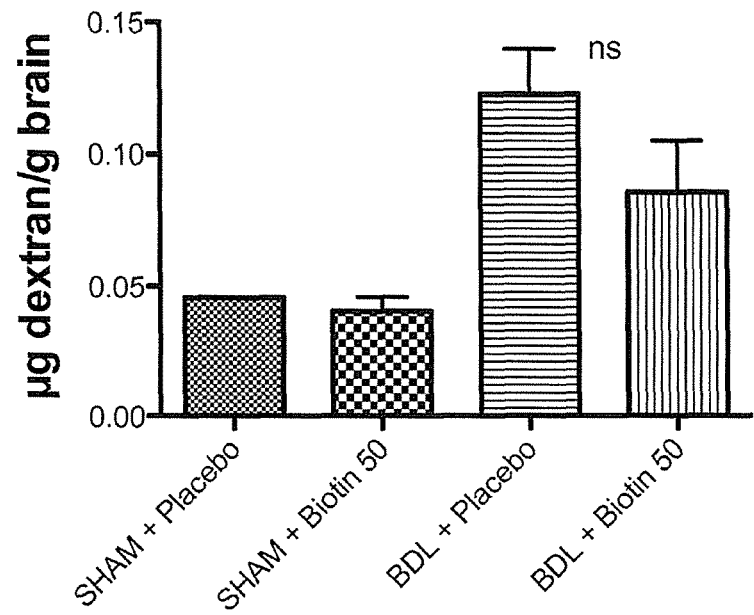
Figure 11A:
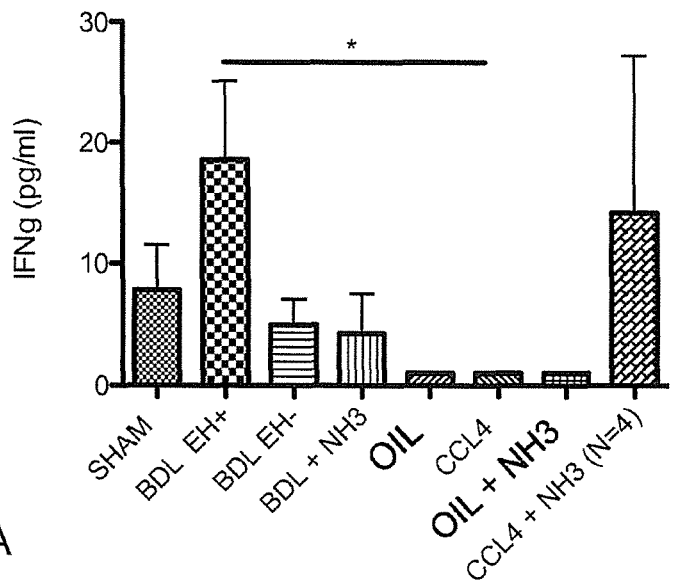
FIG. 11A-B: Measure of serum IFN gamma (FIG. 11A) or TNF alpha (FIG. 11B) in control animals, BDL animals and $CCl_4$ animals with or without NH3-enriched water. HE+: animals showing comportmental signs of hepatic encephalopathy; HE−: animals not showing signs of hepatic encephalopathy.
Figure 11B:
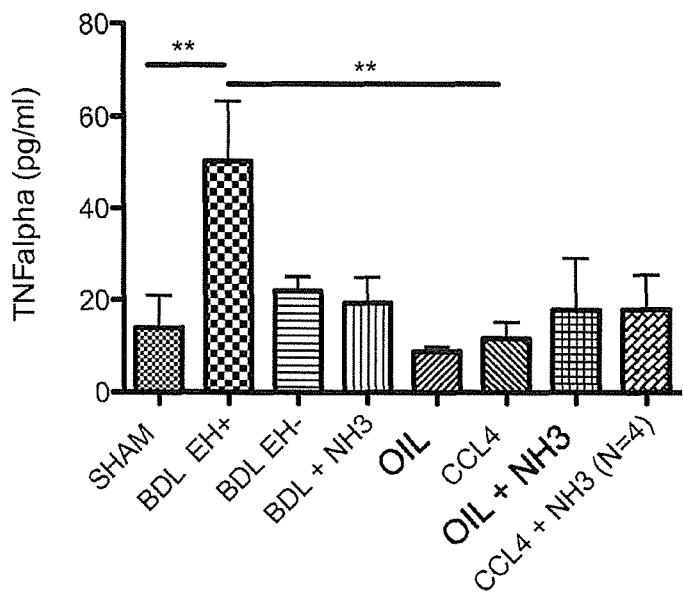
Figure 12A:
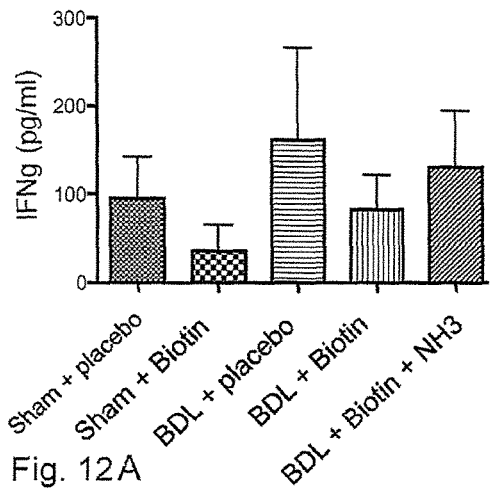
FIG. 12A-C: Measure of serum IFN gamma (FIG. 12A), TNF alpha (FIG. 12B) or IL 6 (FIG. 12C) in control animals, BDL animals with or without NH3-enriched water and/or biotin (300 mg/kg food) enriched diet.
Figure 12B:
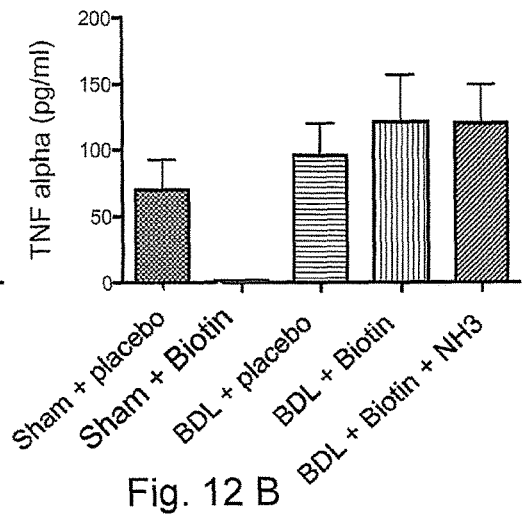
Figure 12C:
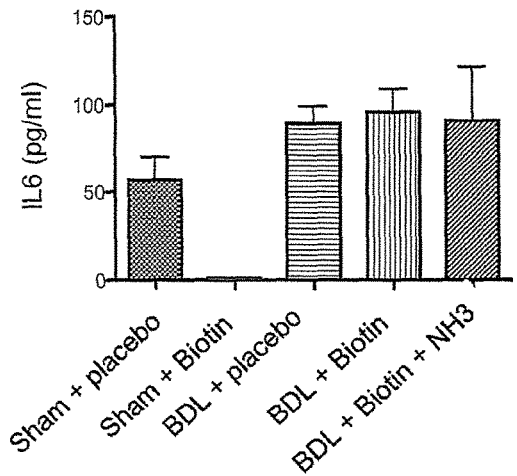

Biotin treatment (300 mg/kg of food) was able to reduce hyperammonemia in BDL rats (FIG. 6; ANOVA, p=0.01).

When biotin is given at a high dose (300 mg/kg of food) to BDL rats, the neurological impairements observed in the OpenField test are reduced compared to BDL rats without biotin. Some of the analysed parameters (total distance travelled, mean speed and duration of activity) are almost normalized in BDL rats treated with biotin as compared to Sham rats. Biotin would therefore prevent HE occurrence if given to BDL rats at a high dose (FIGS. 7A-E and 8A-E showing that a 50 mg/kg of food dose is not high enough to have an effect). The results are similar to those observed with rifaximin or sodium benzoate (not shown).

BDL rats have a significant increase in the intra-cerebral quantity of dextran-TexasRed compared to Sham even when not fed with a NH3-enriched water; this result was not confirmed in $CCl_4$ rats compared to those who received only mineral oil (FIG. 9A-B and 10A-B). This suggests that BDL rats would have an increased blood-brain barrier permeability to solutes.

Treatment with biotin (300 mg/kg of food) was able to normalize intra-cerebral quantity of dextran compared to BDL rats treated with control diet (FIG. 10A-B), while the dose of 50 mg/kg of food did not reach normalization. This suggests that high-dose biotin is able prevent alterations of BBB permeability during HE in cirrhosis Our results show that both BDL and $CCl_4$ rats develop cirrhosis, and both develop hyperammonemia. However, BDL rats displayed HE and had an increased permeability of BBB to solutes, whereas $CCl_4$ rats did not. Differences observed between BDL and $CCl_4$ groups could be due to inflammatory cytokines (FIG. 11A-B and 12A-C). A higher rate of IFNγ and TNFα was observed in BDL rats with HE compared to all the other groups of rats (BDL without HE, Sham, $CCl_4$ and Oil). In BDL rats treated with biotin, IFNγ levels in plasma were decreased. These results seem to confirm that hyperammonemia alone is not sufficient to develop HE during cirrhosis and that inflammation together with hyperammonemia would be required to trigger HE. Biotin would prevent HE both by reducing hyperammonemia and by reducing directly or indirectly inflammatory cytokine production.

To summarize, in BDL rats one can observe a small increase of transaminases (ALAT and ASAT), a large increase of bilirunin and a low decrease of albumin (FIG. 1A-D).

The $CCl_4$ model herein disclosed is different from the $CCl_4$ model disclosed in Nagamine et al or JPH01226814A which is a model of acute hyperammonemia with a single high dose shot. In the present model, small doses of $CCl_4$ are administered to the animals over a few days to more closely mimick a chronic disease. One can observe a very high increase of transaminases, a low increase of bilirubin and no modification of albumin (FIG. 4A-D).

Both animals in the models have increased ammoniemia, but only BDL animals displayed HE, in view of the comportmental alterations, whereas such alterations were not oserved observed in $CCl_4$ animals.

One can further observe that BDL rats have increased BBB permeability, but not $CCl_4$ rats.

Biotin, provided at 30 mg/kg of animal/day (corresponding to a daily dosage of 300 mg in humans), but not biotin provided at 5 mg/kg of animal/day (corresponding to a daily dosage of 50 mg in humans) improves the animal's condition in terms of comportmental improvement and normalization of BBB permeability and would thus prevent development of HE.

From the data reported herein and the figures, it is postulated that biotin acts by decreasing ammonemia and modulating inflammatory profile.

The invention claimed is:

1. A method of administering a composition to a human subject at risk of developing type C Hepatic Encephalopathy, wherein the human subject has been diagnosed with cirrhosis, comprising administering a composition comprising at least 200 mg biotin to said human subject daily.

2. The method of claim 1, wherein the type C Hepatic Encephalopathy is a persistent type C hepatic encephalopathy.

3. The method of claim 1, wherein the type C Hepatic Encephalopathy is an episodic type C hepatic encephalopathy.

4. The method of claim 1, wherein the type C Hepatic Encephalopathy is a minimal type C hepatic encephalopathy.

5. The method of claim 1, wherein the daily amount of biotin administered to the subject is at least 250 mg.

6. The method of claim 1, wherein the daily amount of biotin administered to the subject is at least 300 mg.

7. The method of claim 1, wherein the subject has no clinical sign of Hepatic Encephalopathy before the administration.

8. The method of claim 1, wherein the composition is in a form suitable for oral administration.

9. The method of claim 8, wherein the form suitable for oral administration comprises at least one unit dosage form, wherein each unit dosage form contains at least 20 mg of biotin.

10. The method of claim 1, wherein the composition is in the form of capsules, tablets, lozenges or pills.

11. The method of claim 1, wherein the composition contains biotin and excipients, without any other active ingredient.

12. The method of claim 11, wherein the excipients are selected from the group consisting of talc, microcrystalline cellulose, lactose and mannose.

13. The method of claim 1, wherein the composition is in a form suitable for injectable administration.

14. The method of claim 1, wherein the composition is in the form of a slow release composition.

15. The method of claim 1, wherein said biotin is administered for at least 3 months.

16. The method of claim 1, wherein the daily amount of biotin administered to the subject is above 3 mg/kg.

17. The method of claim 1, further comprising the simultaneous, separate or sequential administration of a therapeutic amount of another drug against type C Hepatic encephalopathy.

18. The method of claim 17, wherein said other drug is selected from the group consisting of Lactulose, lactitol, neomycin, metronidazole, rifaximin, and a combination of L-ornithine and L-aspartate.

19. The method of claim 1, further comprising supplementing the subject's diet with a compound selected from the group consisting of branched-chain amino acids, zinc sulfate, zinc acetate and L-carnitine.

20. The method of claim 1, wherein said human subject has previously experienced an episode of type C Hepatic Encephalopathy.

* * * * *